(12) United States Patent
Rulkov et al.

(10) Patent No.: US 10,610,326 B2
(45) Date of Patent: *Apr. 7, 2020

(54) PASSIVE TAGS, AND SYSTEMS AND METHODS FOR USING THEM

(71) Applicant: CIANNA MEDICAL, INC., Aliso Viejo, CA (US)

(72) Inventors: Nikolai Rulkov, San Diego, CA (US); Michael John Lopez, Irvine, CA (US); John E. Greene, Valley Center, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 1152 days.

This patent is subject to a terminal disclaimer.

(21) Appl. No.: 14/934,019

(22) Filed: Nov. 5, 2015

(65) Prior Publication Data

US 2016/0354177 A1 Dec. 8, 2016

Related U.S. Application Data

(60) Provisional application No. 62/171,804, filed on Jun. 5, 2015.

(51) Int. Cl.
*A61B 90/00* (2016.01)
*H01L 23/60* (2006.01)
(Continued)

(52) U.S. Cl.
CPC .............. *A61B 90/39* (2016.02); *A61B 5/064* (2013.01); *A61B 90/04* (2016.02); *A61B 90/37* (2016.02);
(Continued)

(58) Field of Classification Search
CPC .......... A61B 90/39; A61B 5/064; H01L 23/60
See application file for complete search history.

(56) References Cited

U.S. PATENT DOCUMENTS

| 5,361,070 A | 11/1994 | McEwan |
| 5,573,012 A | 11/1996 | McEwan |

(Continued)

FOREIGN PATENT DOCUMENTS

| EP | 1374793 A1 | 2/2004 |
| EP | 1510183 A1 | 3/2005 |

(Continued)

OTHER PUBLICATIONS http://www.theradarreflectorsite.org/WebManuscript; Chapter 6: Passive Radar Reflector Elements, 18 pages (pp. 64-81).

(Continued)

*Primary Examiner* — Eric D. Bertram
(74) *Attorney, Agent, or Firm* — Stoel Rives LLP

(57) ABSTRACT

Markers, microwave probes, and related systems and methods are provided for localizing lesions within a patient's body, e.g., within a breast. The marker includes an energy converter e.g., one or more photodiodes, for transforming energy pulses striking the marker into electrical energy, a switch, e.g., FET, coupled to the photodiodes such that light from a probe cause the switch to open and close. A pair of antenna wires are coupled to the switch to provide an antenna, the switch configured to open and close when light strikes the photodiodes to modulate signals from the probe reflected by the antenna back to the probe to identify the location of the marker. The marker also includes an electro static discharge (ESD) protection device coupled to the switch to provide protection against an electrostatic discharge event.

15 Claims, 11 Drawing Sheets

(51) Int. Cl.
*A61B 90/98* (2016.01)
*A61B 5/06* (2006.01)
*A61B 34/20* (2016.01)

(52) U.S. Cl.
CPC ............. *A61B 90/98* (2016.02); *H01L 23/60* (2013.01); *A61B 5/062* (2013.01); *A61B 2034/2051* (2016.02); *A61B 2034/2072* (2016.02); *A61B 2090/397* (2016.02); *A61B 2090/3908* (2016.02); *A61B 2090/3941* (2016.02); *A61B 2090/3945* (2016.02); *A61B 2090/3975* (2016.02); *A61B 2090/3979* (2016.02); *A61B 2090/3987* (2016.02); *H01L 2224/48091* (2013.01)

(56) References Cited

U.S. PATENT DOCUMENTS

| | | |
|---|---|---|
| 5,764,162 A | 6/1998 | Ehrlich |
| 5,766,208 A | 6/1998 | McEwan |
| 5,853,366 A | 12/1998 | Dowlatshahi |
| 5,879,357 A | 3/1999 | Heaton et al. |
| 6,144,300 A | 11/2000 | Dames |
| 6,226,548 B1 | 5/2001 | Foley |
| 6,233,479 B1 | 5/2001 | Haddad et al. |
| 6,363,940 B1 | 4/2002 | Krag |
| 6,492,933 B1 | 12/2002 | McEwan |
| 6,496,717 B2 | 12/2002 | Cox et al. |
| 6,575,991 B1 | 6/2003 | Chesbrough et al. |
| 6,725,083 B1 | 4/2004 | Burbank et al. |
| 6,914,552 B1 | 7/2005 | McEwan |
| 7,174,201 B2 | 2/2007 | Govari et al. |
| 7,569,065 B2 | 8/2009 | Chesbrough et al. |
| 7,881,030 B1* | 2/2011 | Li ............ H01Q 21/50 361/111 |
| 8,052,708 B2 | 11/2011 | Chesbrough et al. |
| 9,136,690 B1* | 9/2015 | Upadhyaya ......... H01L 27/0266 |
| 9,713,437 B2* | 7/2017 | Fullerton ............... A61B 5/064 |
| 2003/0004411 A1 | 1/2003 | Govari et al. |
| 2003/0018246 A1 | 1/2003 | Govari et al. |
| 2003/0088186 A1 | 5/2003 | Doody |
| 2003/0192557 A1 | 10/2003 | Krag et al. |
| 2005/0036945 A1 | 2/2005 | Thomas et al. |
| 2005/0059884 A1 | 3/2005 | Krag |
| 2005/0096589 A1 | 5/2005 | Shachar |
| 2005/0163336 A1* | 7/2005 | Hiramoto ............... H04R 19/04 381/369 |
| 2006/0025795 A1 | 2/2006 | Chesbrough et al. |
| 2006/0256981 A1* | 11/2006 | Song ..................... H04R 3/007 381/113 |
| 2006/0258933 A1 | 11/2006 | Ellis et al. |
| 2007/0038014 A1 | 2/2007 | Cox et al. |
| 2007/0093726 A1 | 4/2007 | Leopold et al. |
| 2007/0100666 A1 | 5/2007 | Stivoric |
| 2007/0135711 A1 | 6/2007 | Chernomorsky |
| 2007/0195929 A1 | 8/2007 | Ruchala |
| 2007/0243225 A1 | 10/2007 | McKay |
| 2008/0027313 A1 | 1/2008 | Shachar |
| 2008/0071169 A1 | 3/2008 | Craddock et al. |
| 2008/0086046 A1 | 4/2008 | Petcavich et al. |
| 2008/0200802 A1 | 8/2008 | Bhavaraju et al. |
| 2008/0269601 A1 | 10/2008 | Schwamb |
| 2008/0281190 A1 | 11/2008 | Petcavich et al. |
| 2009/0015832 A1 | 1/2009 | Popovic et al. |
| 2009/0157068 A1 | 6/2009 | Kallel et al. |
| 2009/0216115 A1 | 8/2009 | Seilar |
| 2009/0248014 A1 | 10/2009 | Shachar et al. |
| 2009/0281422 A1 | 11/2009 | Salama et al. |
| 2009/0299174 A1 | 12/2009 | Wright et al. |
| 2010/0234792 A1 | 9/2010 | Dacey |
| 2011/0080678 A1* | 4/2011 | Zhao ................... H01L 27/0285 361/56 |
| 2014/0309522 A1* | 10/2014 | Fullerton ............... A61B 5/064 600/424 |

FOREIGN PATENT DOCUMENTS

| | | |
|---|---|---|
| WO | 0239918 A1 | 5/2002 |
| WO | 2004032779 A1 | 4/2004 |
| WO | 2007087447 A2 | 8/2007 |
| WO | 2007117478 A2 | 10/2007 |

OTHER PUBLICATIONS

Hughes, Jenevieve H. et al., A Multi-site Vlidation Trial of Radioactive Seed Localization as an Alternative to Wire Localization, The Breast Journal, vol. 14 No. 2, 2008 Blackwell Publishing, Inc., 5 pages.

Nilavalan, R. et al., Wideband Microstrip Patch Antenna Desiign for Breast Cancer Tumour Detection, IEEE Xplore/IEEE.org, Apr. 30, 2007, Institution of Engineering and Technology, 1 page.

Stephan, Pam, Wire Localization Procedure—Breast Biopsy or Lumpectomy, About.com/Breast Cancer, Sep. 8, 2008, American Cancer Society/Ohio State Medical Center, 2 pages.

Azevedo, Stephen & Thomas E. McEwan, Micropower Impulse Radar, Science & Technology Review, Jan./Feb. 1996, 7 pages.

Hilger, Ingrid, et al., ultraMEDIS—Ultra-Wideband Sensing in Medicine, INTECH, 2013, 66 pages.

Yun, Xing, et al., Broadband Cross-Polarized Bowtie Antenna . . . , Dept. of Electrical and Computer Engineering, University of Calgary, Calgary, Alberta, CA, 2003 IEEE, pp. 1091-1094, 4 pages.

Shannon, C.J., et al., Dialectric-Filled Slotline Bowtie Antenna for Breast Cancer Detection, Electronics Letters, Mar. 31, 2005, vol. 41, No. 7, 2 pages.

Hagness, Susan C., et al., Three-Dimensional Fdtd Analysis of a Pulsed Microwave Confocal System for Breast Cancer Detection, IEEE Transactions on Antennas and Propagation, vol. 47, No. 5, May 1999, 9 pages.

Krishnan, Sivanand, et al., UWB-IR Active Reflector for High Precision Ranging and Positioning Applications, Institute of Infocomm Research, A*Star Singapore, 2010 IEEE, pp. 14-18, 5 pages.

European Patent Office, Forms PCT/ISA/210, & /237, International Search Report and Written Opinion for Corresponding International Application No. PCT/US2016/035846, Applicant: Cianna Medical, Inc., dated Oct. 25, 2016, 15 pages.

* cited by examiner

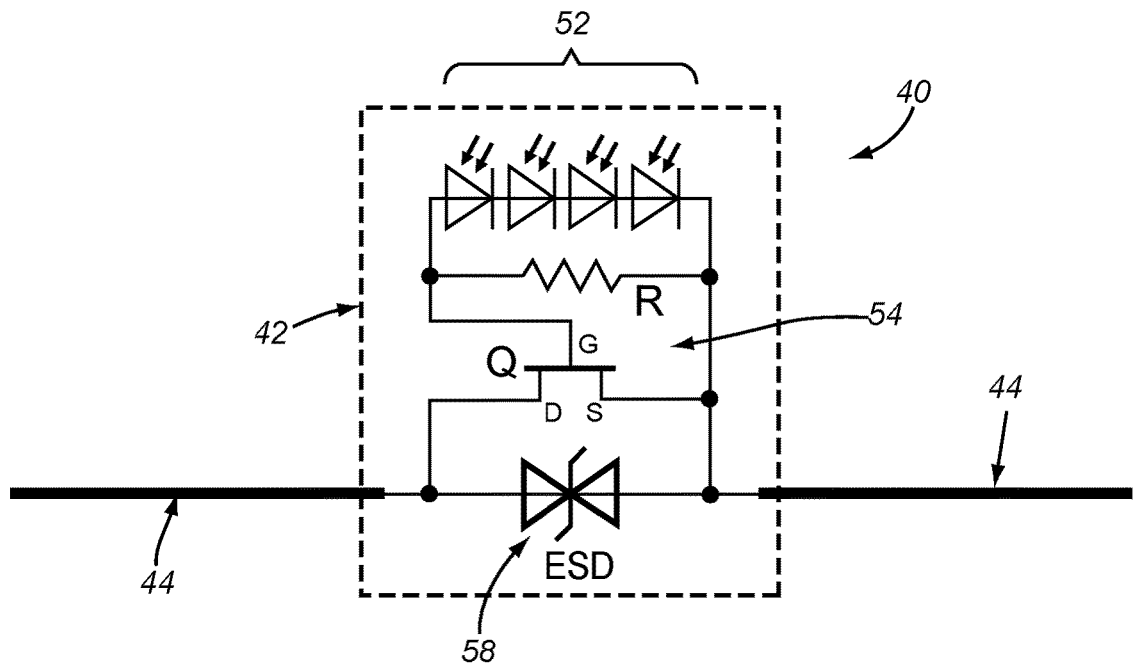
FIG. 2
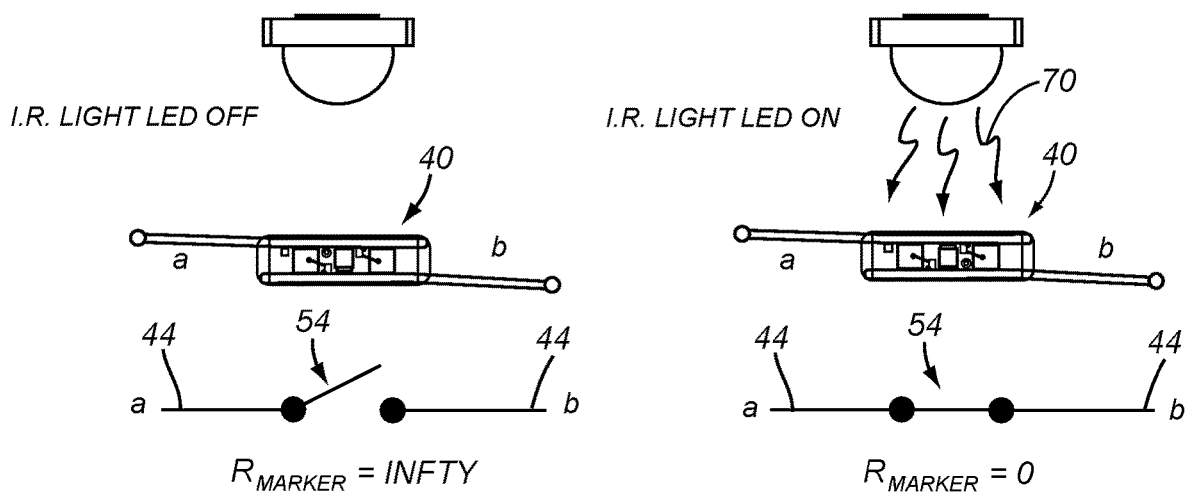
FIG. 3A
FIG. 3B

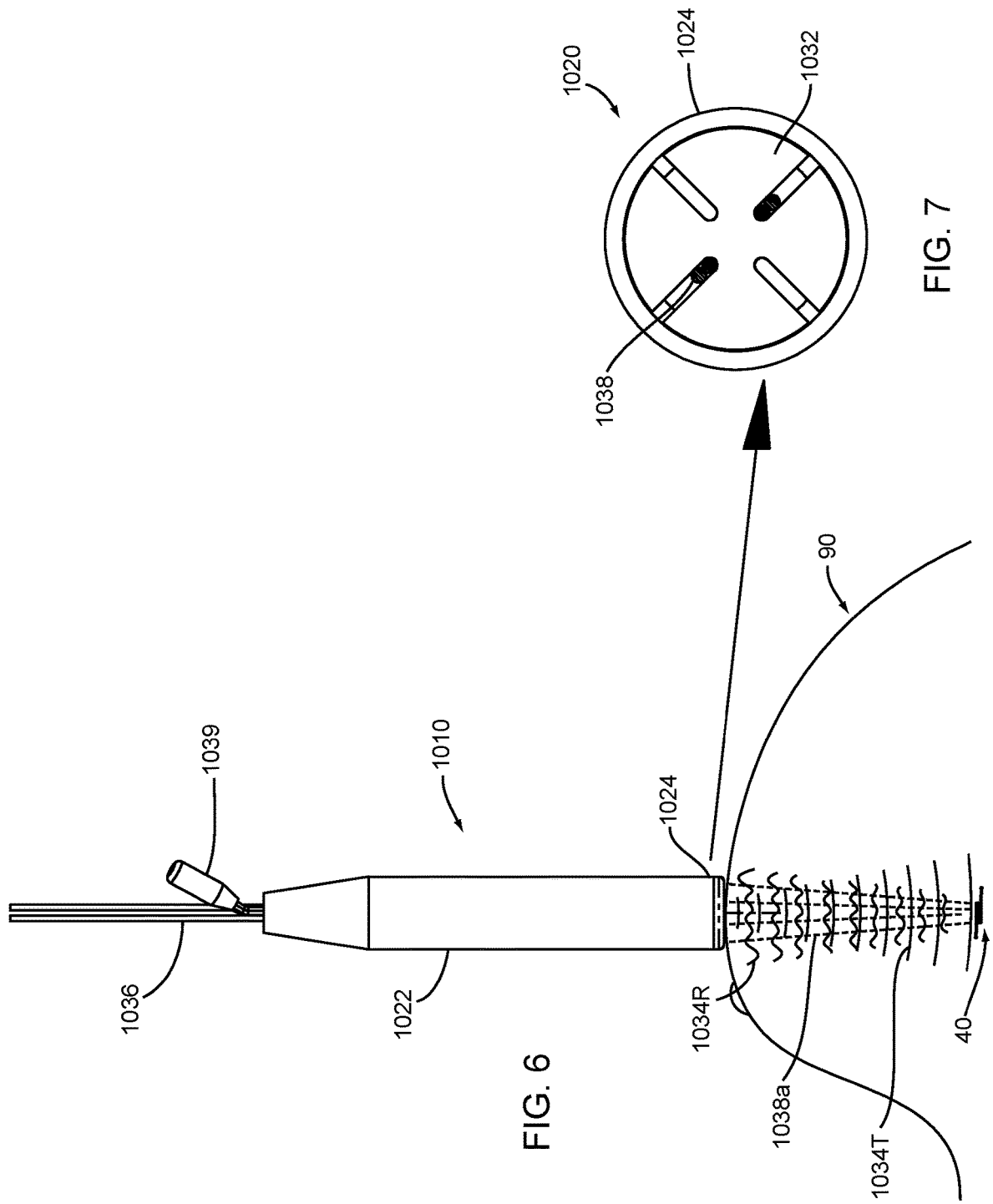

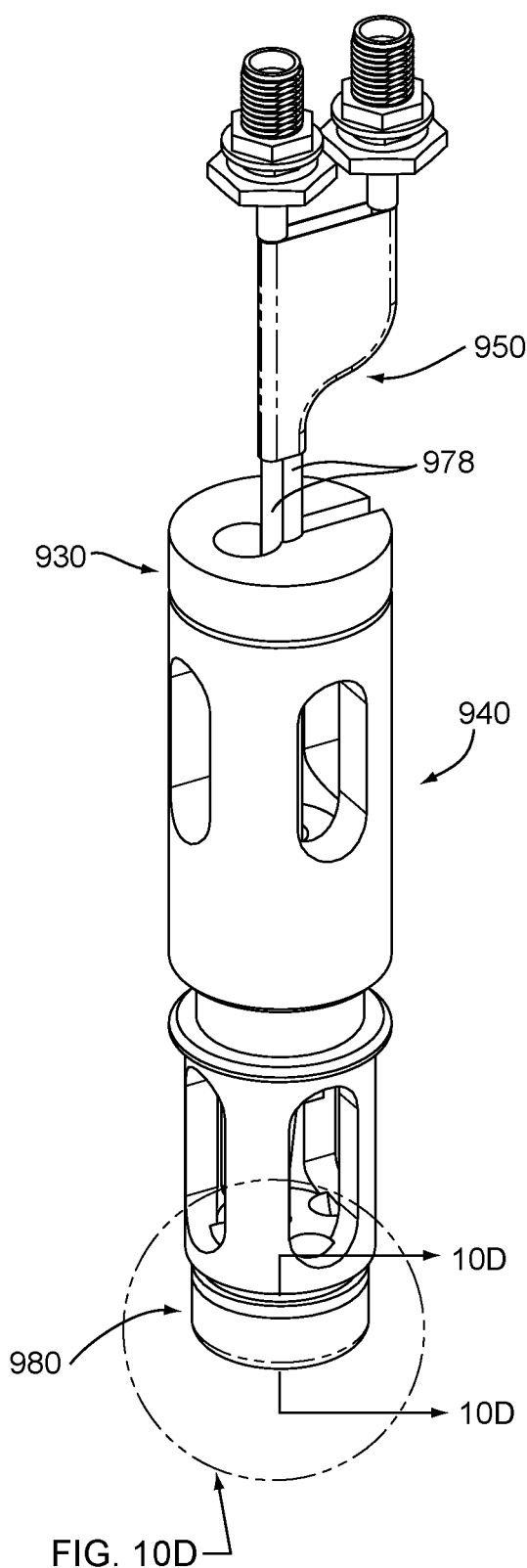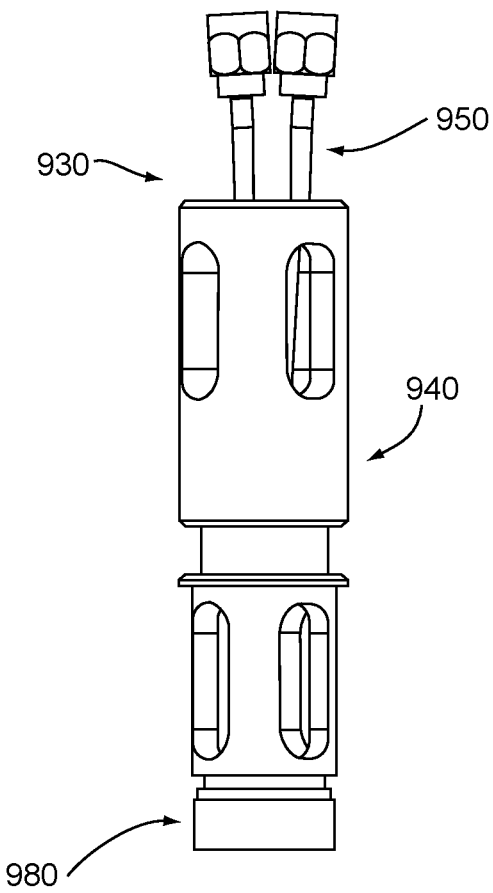
FIG. 10A
FIG. 10B

PASSIVE TAGS, AND SYSTEMS AND METHODS FOR USING THEM

RELATED APPLICATION DATA

The present application claims benefit of provisional application Ser. No. 62/171,804, filed Jun. 5, 2015. The present application is also related to co-pending U.S. application Ser. No. 14/165,253, filed Jan. 27, 2014, which claims benefit of provisional application Ser. No. 61/757,130, filed Jan. 27, 2013, and is also related to co-pending application Ser. No. 13/053,197, filed Mar. 21, 2011, which is a continuation-in-part of Ser. No. 12/824,139, filed Jun. 25, 2010, which claims benefit of provisional patent application Ser. No. 61/220,900, filed Jun. 26, 2009, 61/255,469, filed Oct. 27, 2009, and 61/297,694, filed Jan. 22, 2010. The entire disclosures of these applications and any references cited therein are expressly incorporated by reference herein.

FIELD OF THE INVENTION

The present invention relates to implantable markers or tags, and to systems and methods for localizing such markers within a patient's body, e.g., during surgical procedures or other procedures, such as during lumpectomy procedures.

BACKGROUND

Before a biopsy or surgical procedure to remove a lesion within a breast, e.g., during a lumpectomy procedure, the location of the lesion must be identified. For example, mammography or ultrasound imaging may be used to identify and/or confirm the location of the lesion before the procedure. The resulting images may be used by a surgeon during the procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization, immediately before a procedure, a wire may be inserted into the breast, e.g., via a needle, such that a tip of the wire is positioned at the location of the lesion. Once the wire is positioned, it may be secured in place, e.g., using a bandage or tape applied to the patient's skin where the wire emerges from the breast. With the wire placed and secured in position, the patient may proceed to surgery, e.g., to have a biopsy or lumpectomy performed.

One problem with using a wire for localization is that the wire may move between the time of placement and the surgical procedure. For example, if the wire is not secured sufficiently, the wire may move relative to the tract used to access the lesion and consequently the tip may misrepresent the location of the lesion. If this occurs, when the location is accessed and tissue removed, the lesion may not be fully removed and/or healthy tissue may be unnecessarily removed. In addition, during the procedure, the surgeon may merely estimate the location of the wire tip and lesion, e.g., based on mammograms or other images obtained during wire placement, and may proceed with dissection without any further guidance. Again, since such images are two dimensional, they may provide limited guidance to localize the lesion being treated or removed.

Alternatively, it has been suggested to place a radioactive seed to provide localization during a procedure. For example, a needle may be introduced through a breast into a lesion, and then a seed may be deployed from the needle. The needle may be withdrawn, and the position of the seed may be confirmed using mammography. During a subsequent surgical procedure, a hand-held gamma probe may be placed over the breast to identify a location overlying the seed. An incision may be made and the probe may be used to guide excision of the seed and lesion.

Because the seed is delivered through a needle that is immediately removed, there is risk that the seed may migrate within the patient's body between the time of placement and the surgical procedure. Thus, similar to using a localization wire, the seed may not accurately identify the location of the lesion, particularly, since there is no external way to stabilize the seed once placed. Further, such gamma probes may not provide desired precision in identifying the location of the seed, e.g., in three dimensions, and therefore may only provide limited guidance in localizing a lesion.

Accordingly, apparatus and methods for localization of lesions or other tissue structures in advance of and/or during surgical, diagnostic, or other medical procedures would be useful.

SUMMARY

The present invention is directed to implantable markers and tags, and to systems and methods for localizing such markers within a patient's body, e.g., during surgical procedures or other procedures, such as during lumpectomy procedures.

In accordance with one embodiment, a marker is provided sized for introduction into a target tissue region within a patient's body that includes an energy converter for transforming energy pulses striking the marker into electrical energy; a switch coupled to the energy converter such that the energy pulses cause the switch to open and close; a pair of elongate wires coupled to the switch to provide an antenna, the switch configured to open and close to modulate signals reflected by the antenna back to a source of the signals; and an electro static discharge (ESD) protection device coupled to the switch to provide protection against an electrostatic discharge event.

In accordance with another embodiment, a marker is provided for introduction into a target tissue region within a patient's body that includes a field effect transistor (FET); one or more photosensitive diodes coupled in series across a source and a gate of the FET to convert light pulses received from a light source to generate a voltage to open and close the FET; a pair of elongate wires coupled to a drain and the source of the FET to provide an antenna, the FET configured to open and close to modulate signals reflected by the antenna back to a source of the signals; and an electro static discharge (ESD) protection device coupled between the drain and the source of the FET to set a maximal voltage between the drain and the source.

In accordance with still another embodiment, a system is provided for localizing a marker within a body that includes a marker including an energy converter; a probe comprising a transmit antenna configured to transmit a transmit signal into the body towards the marker, a receive antenna configured to receive a receive signal that is reflected from the marker, and an energy source for delivering energy pulses into the body to open and close the switch and modulate signals reflected by the marker back to the receive antenna; a processor coupled to the receive antenna for locating or otherwise detecting the marker within the body based at least in part on the modulated signals reflected by the marker; and a display to present information representing the distance from the tip of the probe to the marker and/or other information related to the location of the marker within the patient's body. In an exemplary embodiment, the energy source may include a light source, and the energy converter may include one or more photosensitive diodes configured to convert light from the light source to generate a voltage.

In one embodiment, the voltage may open and close a switch in the marker to modulate an antenna of the marker to modulate the signals reflected by the marker. In addition, the marker may include an electro static discharge (ESD) protection device coupled to the switch to provide protection against an electrostatic discharge event. In another embodiment, the voltage may intermittently induce a current in a conductor loop of the marker, which may modulate the signals reflected by the marker.

In accordance with yet another embodiment, a system is provided for localization of a target tissue region within a patient's body that includes a probe including one or more antennas for transmitting electromagnetic signals into a patient's body and receiving reflected signals from the patient's body, and an energy source for delivering energy pulses into a patient's body. The system also includes a marker sized for implantation within a patient's body, the marker including an energy converter configured to transform the energy pulses from the energy source into electrical energy, and a switch coupled to the energy converter such that the energy pulses cause the switch to open and close to modulate the electromagnetic signals from the probe reflected by the marker, and an electro static discharge (ESD) protection device coupled to the switch to provide protection against an electrostatic discharge event.

In accordance with another embodiment, a method is provided for localization of a target tissue region within a patient's body that includes implanting a marker within a patient's body, the marker including a switch, an energy converter, and an electro static discharge (ESD) protection device; placing a probe adjacent the patient's body oriented towards the marker; and activating the probe to a) transmit electromagnetic signals into the patient's body, b) receive reflected signals from the patient's body, and c) deliver energy pulses into the patient's body such that the energy converter transforms the energy pulses into electrical energy to open and close the switch to modulate the electromagnetic signals from the probe reflected by the marker, and wherein the ESD protection device provides protection against an electrostatic discharge event. In an exemplary embodiment, delivering energy pulses into the patient's body may include delivering infrared light into the patient's body, and the energy converter may include one or more photosensitive diodes that transform the infrared light into electrical energy to open and close the switch to modulate the electromagnetic signals from the probe reflected by the marker. In addition, the probe may provide information related to the location of the marker within the patient's body and/or relative to the probe.

In one embodiment, the method may include using an electrical tool adjacent the marker, and the ESD protection device may be activated when electrical energy from the tool exceeds a maximal voltage for the switch.

In accordance with still another embodiment, a system is provided for localization of a target tissue region within a patient's body that includes a probe including one or more antennas for transmitting electromagnetic signals into a patient's body and receiving reflected signals from the patient's body, and a light source for delivering light pulses into a patient's body. The system also includes a marker sized for implantation within a patient's body, the marker including one or more photosensitive diodes coupled to a conductor loop configured to transform the light pulses from the light source into electrical energy to induce a current in the conductor loop and modulate the electromagnetic signals from the probe reflected by the marker.

In accordance with yet another embodiment, a method is provided for localization of a target tissue region within a patient's body that includes implanting a marker within a patient's body, the marker including one or more photosensitive diodes coupled to a conductor loop; placing a probe adjacent the patient's body oriented towards the marker; and activating the probe to a) transmit electromagnetic signals into the patient's body, b) receive reflected signals from the patient's body, c) deliver light pulses into the patient's body such that the one or more photosensitive diodes transform the light pulses into electrical energy to induce a current in the conductor loop and modulate the electromagnetic signals from the probe reflected by the marker, and d) provide an output related to the location of the marker within the patient's body.

Other aspects and features of the present invention will become apparent from consideration of the following description taken in conjunction with the accompanying drawings.

BRIEF DESCRIPTION OF THE DRAWINGS

These and other features, aspects, and advantages of the present disclosure will become better understood with regard to the following description, appended claims, and accompanying drawings where:

FIG. 2 is an exemplary embodiment of a schematic of a circuit that may be included in the marker of FIG. 1.

FIGS. 3A and 3B are schematics demonstrating operation of a switch of the circuit of FIG. 2.

FIG. 6 is a side view of an exemplary embodiment of a probe and a target implanted within a breast.

FIG. 7 is an end view of a distal end of the probe of FIG. 62.

FIGS. 10A and 10B are perspective and side views, respectively, of another exemplary of an antenna probe that may be included in a system such that shown in FIGS. 7-9.

DETAILED DESCRIPTION OF THE EXEMPLARY EMBODIMENTS

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 1:
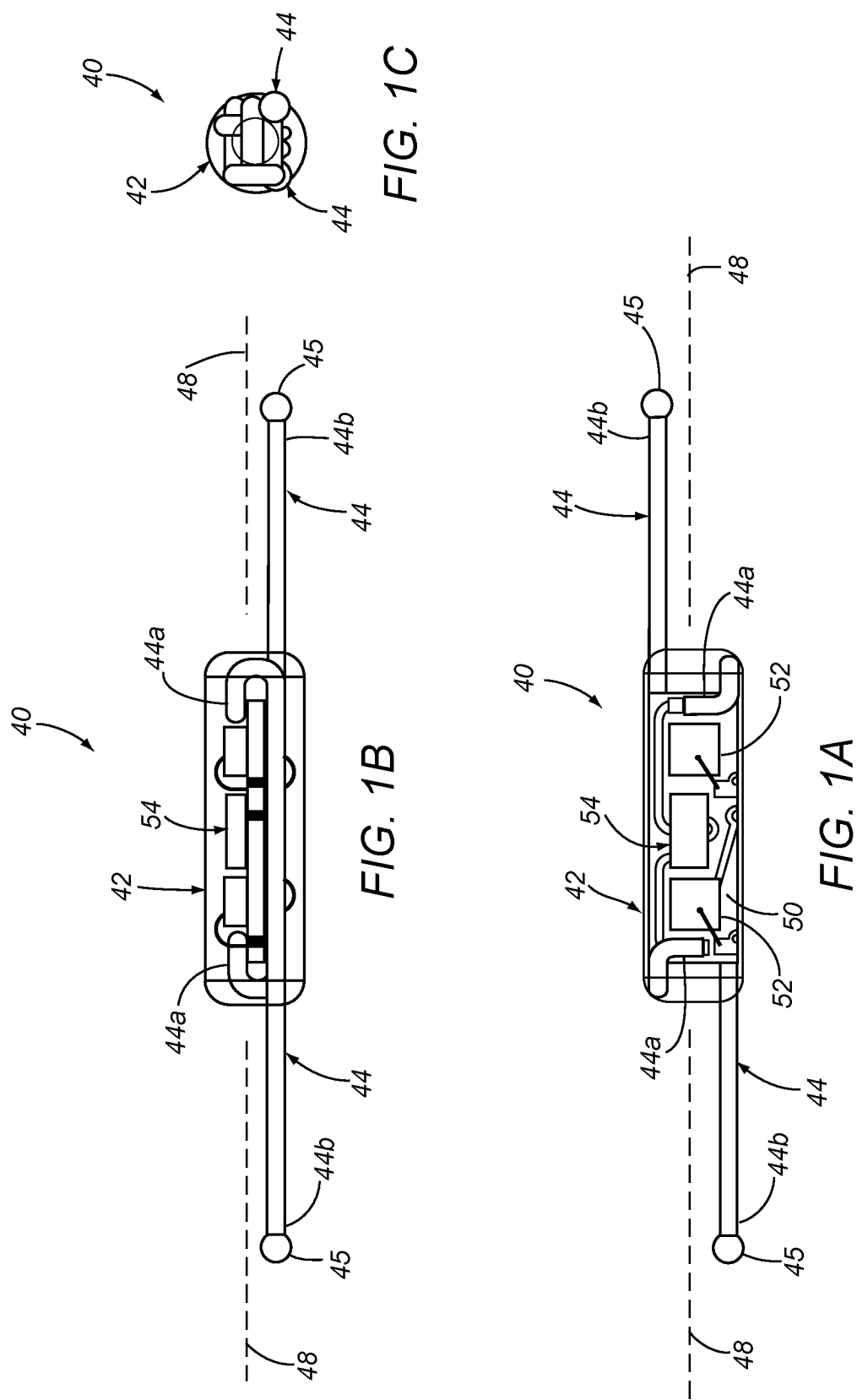
FIGS. 1A-1C are top, side, and end views, respectively, of an exemplary embodiment of a marker for implantation within a patient's body.
Figure 8:
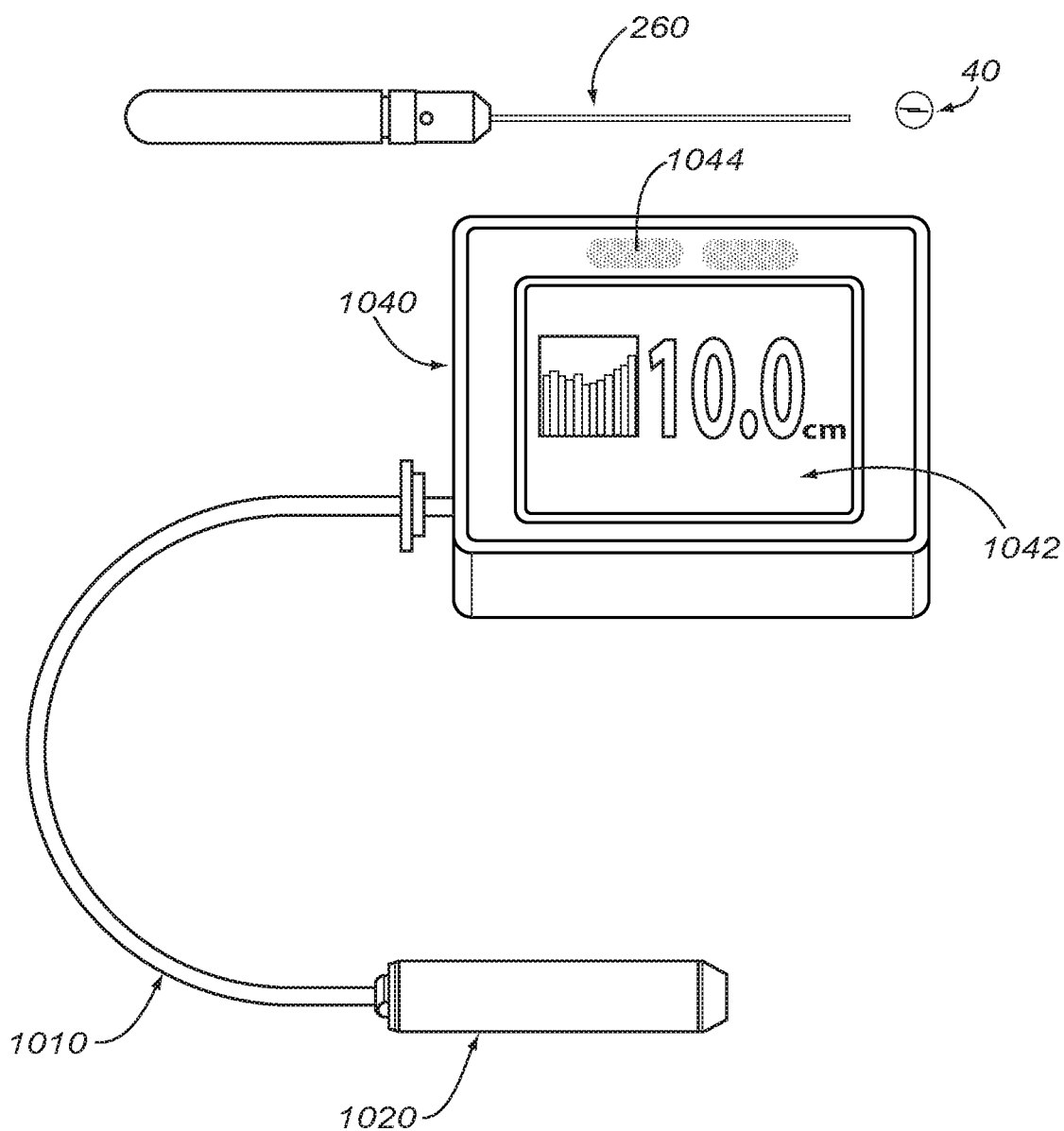
FIG. 8 is a schematic representation of exemplary components of a system for localizing a marker.

Turning to the drawings, FIGS. 1A-1C show an exemplary embodiment of a passive marker or tag 40 that may be implanted within a patient's body, such as within a breast 90, e.g., as shown in FIG. 6. Generally, the marker 40 includes an electronics package 42 coupled to a pair of wires or antennas 44. The marker 40 may be included in a system 1010 for performing a procedure, such as a lumpectomy procedure, e.g., including a delivery device 260 for delivering one or more of the markers into tissue, a probe 1020 for locating marker(s) implanted within tissue, and/or other components, e.g., as shown in FIGS. 6-8 and described further below.

In an exemplary embodiment, each wire 44 may be an elongate member, e.g., a solid or hollow structure having a diameter or other maximum cross-section between about half and two millimeters (0.5-2 mm) and a length between about one and ten millimeters (1.0-10 mm). The wires 44 may be formed from elastic or superelastic material and/or from shape memory material, e.g., stainless steel, Nitinol, and the like, such that the wires 44 are biased to a predetermined shape when deployed within tissue, but may be elastically deformed, e.g., to facilitate delivery, as explained elsewhere herein. Alternatively, the wires 44 may be substantially rigid such that the marker 40 remains in a substantially fixed, e.g., linear or curved, shape. As described elsewhere herein, the wires 44 may act as antennas and/or otherwise cooperate with electrical components within the electronics package 42.

Optionally, the wires 44 may carry one or more beads or other elements (not shown), e.g., similar to embodiments described in the applications incorporated by reference herein. For example, the wires 44 may provide core wires that carry a plurality of beads or segments (not shown) including multiple surfaces, angles, and/or edges to enhance detection of the marker 40. In an exemplary embodiment, the beads may include a plurality of individual annular bodies, e.g., each defining a portion of a generally cylindrical or spherical shape. The beads may be formed from desired materials, e.g., metals, such as stainless steel, Nitinol, titanium, and the like, plastic materials, or composite materials, as described in the applications incorporated by reference herein. During assembly, a plurality of beads may be placed over and secured to the wires 44, e.g., before or after attaching the wires 44 to the electronics package 42, e.g., as described in the applications incorporated by reference herein.

As shown in FIGS. 1A-1C, the wires 44 may be biased to assume a substantially linear configuration, e.g., such that the wires 44 extend substantially parallel to a longitudinal axis 48 of the marker 40. Optionally, one or both wires 44 may be offset from the longitudinal axis 48, which may enhance loading the marker 40 within a delivery device (not shown), as described elsewhere herein.

As shown, each wire 44 may include a first end 44a coupled to a printed circuit board (PCB) or other circuit 50 within the package 42 and a second free end 44b terminating in an enlarged and/or rounded tip 45. Optionally, the first ends 44a may include one or more bends, e.g., to facilitate coupling the first ends 44a to the circuit 50 and/or such that the wires 44 extend tangentially from opposite sides of the package 42, as best seen in FIG. 1A.

Alternatively, the wires 44 may be biased to assume a curvilinear or other configuration, e.g., a helical, serpentine or other curved shape, around the longitudinal axis 48. For example, the wires 44 may be formed from elastic or superelastic material that is shape set such that the wires 44 are biased to the helical configuration shown, yet may be resiliently straightened to a substantially linear configuration, e.g., to facilitate loading the marker 40 into a delivery device and/or otherwise introducing the marker 40 into a patient's body, e.g., as described in the applications incorporated by reference herein.

With additional reference to FIG. 2, the marker 40 may include one or more circuits or other electrical components 50 encased or embedded in the electronics package 42 and configured to modulate incident signals from a probe (not shown, such as the probe 1020 shown in FIG. 6 and described elsewhere herein) used to locate the marker 40, also as described elsewhere herein. In an exemplary embodiment, best seen in FIG. 1A, a semiconductor chip, print circuit board (PCB), and/or other circuit 50 may be carried in the package 42 that includes a voltage or power source or other power or energy converter 52, a switch 54 that may be opened and closed when the energy converter 52 generate electrical energy, and an Electro Static Discharge (ESD) protection device 58.

In an exemplary embodiment, the energy converter 52 includes a plurality of photosensitive diodes capable of transforming incident light (e.g., infrared light) striking them into electrical energy (e.g., a predetermined minimum voltage). As shown, multiple pairs of diodes 52 may be connected in series, which may be arranged orthogonally to one another spatially within the package 42. For example, given that photosensitive diodes are directional, at least two pairs of diodes 52 may be mounted within the package 42 offset one hundred eighty degrees (180°) or otherwise relative to one another, e.g., as best seen in FIG. 1A, such that at least one pair of diodes 52 may receive light from a light transmitter of the probe 1020 regardless of the orientation of the marker 40 relative to the probe 1020 after implantation. The package 42 may be at least partially transparent or the diodes 52 may be exposed such that light directed towards the package 42 may be received by the diodes 52.

In alternative embodiments, the energy converter 52 may include other components capable of transforming external energy into a desired voltage. For example, if the probe 1020 includes another power source, e.g., a source of EMF, RF, or vibrational energy, the energy converter 52 may include a pick-up coil, antenna, or other device capable of transforming the incident energy into the desired voltage, e.g., including a capacitor and/or other components arranged to deliver the desired voltage to the switch 54. One advantage of infrared energy is that it may pass sufficiently through tissue such that a probe 1020 placed against a patient's skin may deliver sufficient energy to activate a relatively small marker 40 implanted several inches away within the patient's body, e.g., breast 90, as shown in FIG. 6.

In the embodiment shown in FIG. 2, the switch 54 may be a field effect transistor (FET), e.g., a junction field effect transistor (JFET), with one end of the diodes 52 coupled to the gate (G) and the other coupled to the source (S), with a resistor 56 coupled between the gate (G) and the source (S), e.g., to discharge the diodes 52 when there is no IR light. In an exemplary embodiment, the switch 54 may include an enhancement mode pseudomorphic high electron mobility transistor (E-pHEMT), such as a VMMK-1225 manufactured by Avago Technologies US Inc., and the resistor 56 may be a three mega-Ohm (3 MΩ) resistor. In an alternative embodiment, the switch 54 may be a Schottky diode coupled to the diodes 52 (or other voltage source), e.g., with opposite ends of the diode coupled to the wires 44.

Also as shown, the source (S) of the switch 54 may be electrically coupled to one of the wires 44 and the drain (D) may be coupled to the other wire 44, e.g., such that the wires 44 provide an antenna for the marker 40. For example, the components of the circuit 50 may be mounted within the package 52 such that the components are electrically isolated from one another other than as coupled in the schematic of FIG. 2. The wires 44 may be bonded or otherwise attached to the package 52 such that ends of the wires 44 are electrically coupled to the switch 54 as shown.

Each diode 52 may be capable of generating sufficient voltage (e.g., about a half Volt (0.5 V)) when exposed to light to open and close the switch 54 when there is little or no load (i.e., current draw). Since the circuit 50 is intended to be merely modulate signals from the probe 1020, little or no current is needed, and so the power required from the diodes 52 (and consequently from the probe 1020) may be minimal, thereby reducing power demands of the marker 40 and probe 1020.

With additional reference to FIGS. 3A and 3B, light intermittently striking the diodes 52 may generate a voltage across the gate (G) and source (S) to provide a control signal that may open and close the switch 54. For example, FIG. 3A shows the switch 54 in the open configuration when infrared light is absent, while FIG. 3B shows the switch 54 in the closed configuration when infrared light 70 strikes the diodes 52, thereby connecting both wires 44 together. Thus, the result is that the marker 40 provides a passive tag that includes what equates to a high-frequency switch in the middle of the marker 40. By being able to change the switch 54 from closed to open, the reflection properties of the antenna provided by the wires 44 may be changed significantly. For example, the switch 54 may change the polarity or otherwise modulate signals reflected from the marker 40 as the switch 54 is opened and closed.

Some of the challenges involved in detecting markers implanted within breast tissue (or elsewhere in a patient's body) include the relatively small radar cross-section (RCS) of such markers and contamination of the received reflected signal, e.g., due to (a) scattering caused by tissue inhomogeneity; (b) cross-talk between transmit and receive antennas of the probe; and (c) signal distortions due to near field effects and other factors. To deal with these complicating factors and distinguish the reflected marker signal from contaminating signals received by the probe, the switch 54 provides periodic modulation of reflective properties of the marker 40.

Specifically, the marker 40 is made to periodically change its structure between two form factors, e.g., the reflectors shown in FIGS. 3A and 3B. For example, as described further elsewhere herein, digital signal processing of the received signals using ultra-wideband (UWB) radar uses synchronous detection of the signal modulated with marker switching frequency. This significantly increases the signal-to-noise (SNR) on the marker signal because other contaminating signals remain unchanged within the modulation period. To provide a mechanism for a synchronous detector, the marker switching process is controlled in the probe 1020 by illuminating breast tissue with near infrared (IR) light pulses that are received by the marker 40.

Switching of the marker reflective form-factor is controlled with the set of diodes 52 operating in photovoltaic mode. When the diodes 52 receive light from the probe 102 (represented by arrows 70 in FIG. 3B), the diodes 52 generate voltage that is applied between the gate (G) and source (S) of the switch 54, which closes and connects together the drain (D) and source (S) making both antenna wires 44 connected together, as shown in FIG. 3B. When the light is off, the switch 54 is open and the drain (D) and source (S) are electrically disconnected, as shown in FIG. 3A.

In addition, the ESD device 58 may be coupled in parallel across the switch 54, e.g., between the drain (D) and source (S), to provide protection against an electrostatic discharge event. For example, use of an E-pHEMT device as switch 54 sets restrictions on the absolute maximal voltage between the drain (D) and source (S) and, therefore, across the marker's antennas. In the exemplary embodiment of a VMMK-1225 E-pHEMT, the maximal voltage across the switch 54 may be no more than about five Volts (5 V). Modern breast surgery often involves the use of electrocutting tools, electocautery tools, and/or other tools (not shown), which can generate electrical pulses of a few kV. If such a tool gets close to the marker 40, the tool can cause a very large voltage across antenna wires 44 and destroy the switch 54.

To increase survivability of the marker 40 during operation of such tools, the ESD protection device 58 truncates voltage on the switch 58 device when the voltage approaches the maximal value. Generally, the ESD protection device 58 in the marker 40 should have low capacitance that does not shunt the antennas 44 for the frequency range of the small amplitude UWB signal coming from the signals from the probe 1020. In exemplary embodiments, the ESD protection device 58 may be a transient voltage suppressor, such as a Zener diode, a low-capacitance varistor, and the like.

Figure 4:
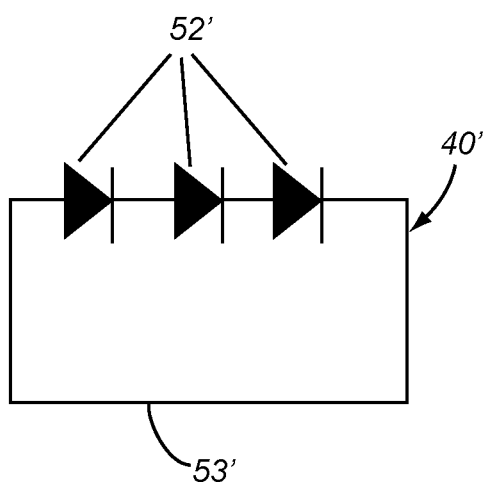
FIG. 4 is a schematic of another exemplary embodiment of a marker for implantation within a patient's body

Turning to FIG. 4, an alternative embodiment of a passive marker 40' is shown that includes a plurality of photosensitive diodes 52' connected in series and the resulting output is coupled to a conductor loop 53.' The resulting current loop is modulated by a light trigger, e.g., using the probe 1020 similar to the marker 40, for synchronous detection. When the light triggers the photodiodes 52,' current is induced in the conductor path of the conductor loop 53,' thereby modulating the reflective characteristics of the marker 40,' e.g., changing the scattering characteristics of the marker 40.' The probe 1020 may subtract the difference between the two states of the marker 40' and use the difference for synchronous detection.

Figure 5A:
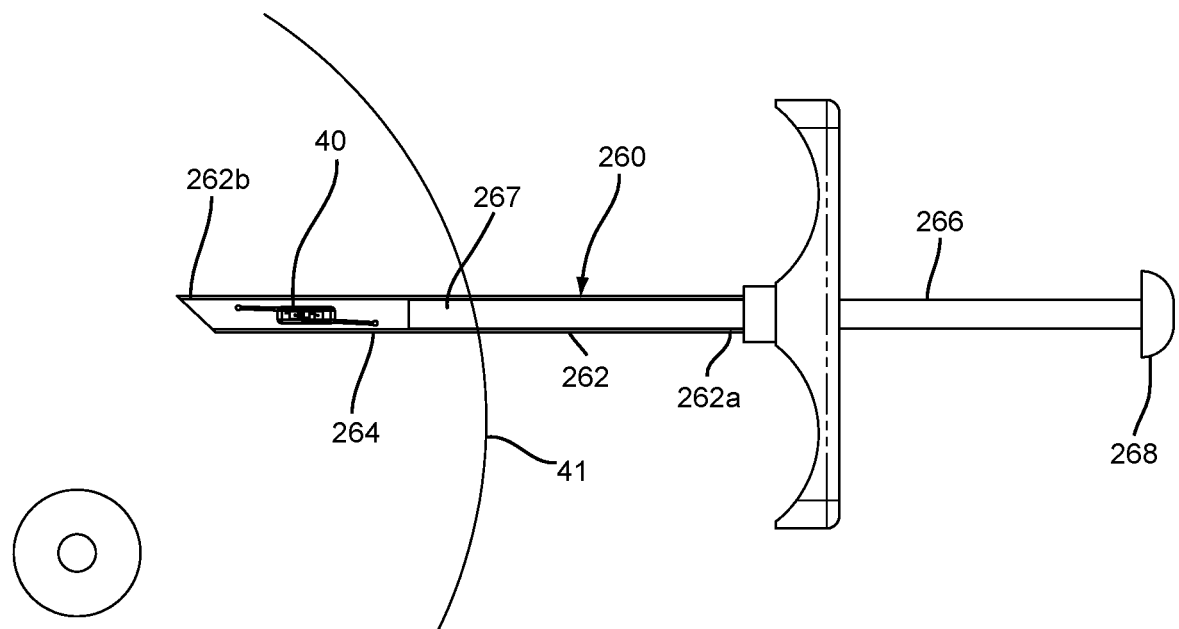
FIGS. 5A and 5B are side views of a breast, showing a delivery device being used to deliver a marker into tissue within the breast.
Figure 5B:
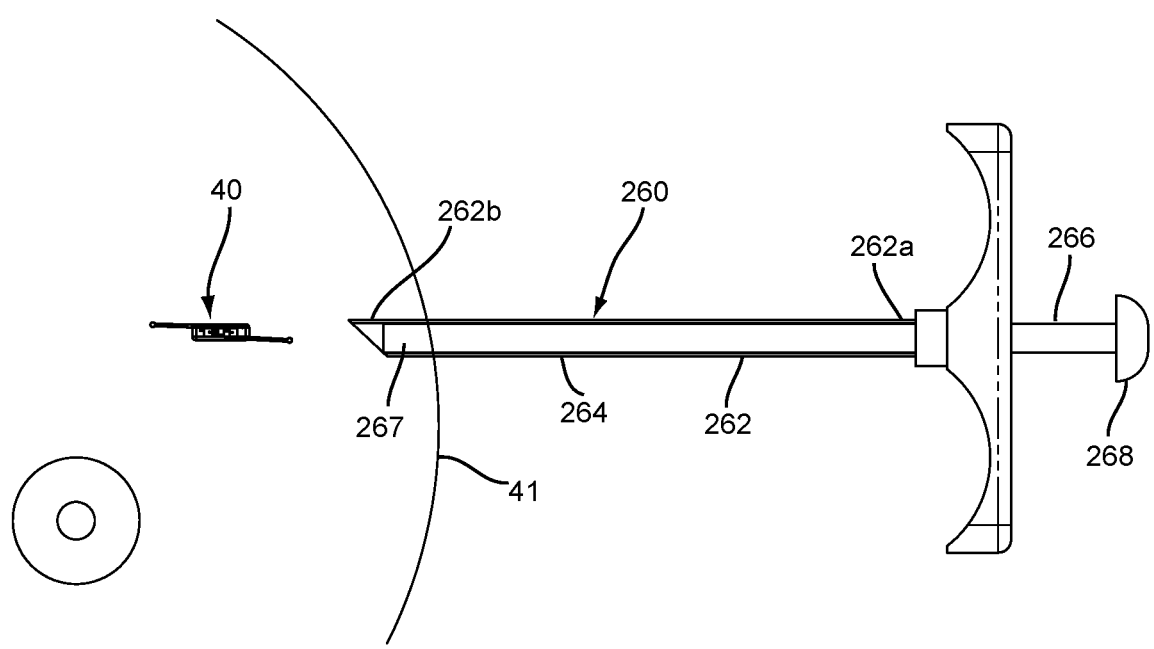

Optionally, as shown in FIGS. 5A and 5B, a needle or delivery device 260 may be provided for introducing one or more markers 40 or 40' (one marker 40 shown) into a patient's body, e.g., similar to any of the embodiments described in the applications incorporated by reference elsewhere herein. For example, the delivery device 260 may include a shaft 262 including a proximal end 262a and a distal end 262b sized for introduction through tissue into a target tissue region (not shown) and carrying the marker(s) 40. The delivery device 260 may include a lumen 264 extending at least partially between the proximal and distal ends 262a, 262b of the shaft 262, and a pusher member 266 slidable within the shaft 262 for selectively delivering one or more markers 40 successively or otherwise independently from the lumen 264.

As shown, the distal end 262b of the shaft 262 may be beveled, pointed, and/or otherwise sharpened such that the shaft 262 may be introduced directly through tissue. Alternatively, the delivery device 260 may be introduced through a cannula, sheath, or other tubular member (not shown) previously placed through tissue, e.g., as described in the applications incorporated by reference herein. Optionally, the distal end 262b may include a band or other feature, e.g., formed from radiopaque, echogenic, or other material, which may facilitate monitoring the distal end 262b during introduction, e.g., using fluoroscopy, ultrasound, electromagnetic signals, and the like.

As shown, the pusher member 266 includes a piston or other element (not shown) disposed within the lumen 264 adjacent the marker(s) 40 and a plunger or other actuator 268 coupled to the piston to push the marker(s) 40 from the lumen 264. For example, as shown in FIG. 5A, the distal end 262a of the shaft 262 (carrying the marker 40 therein) may be inserted into the breast 41 (or other tissue) and advanced or otherwise positioned to place the marker 40 at a target location, e.g., within a cancerous lesion (not shown). Optionally, external imaging may be used to confirm the location of the marker 40 relative to the lesion. Once at the target location, the shaft 262 may be withdrawn relative to the pusher member 266, thereby deploying the marker 40, as shown in FIG. 5B. Optionally, the delivery device 260 may carry multiple markers (not shown), and the shaft 262 may be repositioned one or more times to deploy additional markers.

Alternatively, if desired, the pusher member 266 may be advanced to deploy the marker(s) 40 successively from the lumen 264, rather than retracting the shaft 262. In another alternative, a trigger device or other automated actuator (not shown) may be provided on the proximal end 262a of the shaft 262, which may retract the shaft 262 sufficiently with each activation, e.g., to delivery an individual marker 40 from the distal end 262b, e.g., as described in the applications incorporated by reference herein.

Optionally, one or both of the wires 44 may be offset from the longitudinal axis 48 to facilitate delivery of the marker(s) 40. For example, one wire 44 may extend substantially parallel to the longitudinal axis 48 while the other wire 44 may define a predetermined acute angle relative to the longitudinal axis 48 such that the tips 45 of the wires 44 slidably engages an inner surface of the delivery device 260, e.g., with sufficient friction to prevent the marker 40 from freely falling out of the lumen 264 unless the shaft 262 is refracted relative to the pusher member 266 with sufficient force to overcome the friction.

Turning to FIGS. 6-9, an exemplary embodiment of a system 1010 is shown for localization of a target tissue region within a patient's body, such as a tumor, lesion, or other tissue structure within a breast 90 or other location within a body. As shown in FIG. 8, the system 1010 generally includes a delivery device 260 carrying one or more targets, tags, or markers 40 (one shown), a probe 1020 for detecting and/or locating the marker 40, e.g., using ultra-wideband radar, e.g., and a controller and/or display unit 1040 coupled to the probe 1020, e.g., using one or more cables 1036, similar to embodiments described in the applications incorporated by reference herein.

For example, the probe 1020 may be a portable device having electromagnetic signal emitting and receiving capabilities, e.g., a micro-power impulse radar (MIR) probe, similar to embodiments described in the applications incorporated by reference herein. As shown in FIG. 6, the probe 1020 may be a handheld device including a first or distal end 1024 intended to be placed against or adjacent tissue, e.g., a patient's skin or underlying tissue, and a second or proximal end 1022, e.g., which may be held by a user. Generally, the probe 1020 includes one or more antennas, e.g., a transmit antenna and a receive antenna (not shown) mounted on a ceramic disk 1032 (shown in FIG. 7). In addition, the probe 1020 includes a light transmitter, e.g., a plurality of light fibers 1038 (shown in FIG. 7), configured to transmit light pulses (represented by dashed lines 1038a in FIG. 6) into tissue contacted by the distal end 1024, e.g., into breast tissue 90, as shown in FIG. 6. The light fibers 1038 may be coupled to a light source (not shown), e.g., by coupling 1039, such that light from the light source passes through the light fibers 1038 distally from the distal end 1024 of the probe 1020.

In an exemplary embodiment, the light source is an infrared light source, e.g., capable of delivering near infrared light between, for example, eight hundred and nine hundred fifty nanometers (800-950 nm) wavelength. Optionally, the light fibers may include one or lenses, filters, and the like (not shown), if desired, for example, to focus the light transmitted by the probe 1020 in a desired manner, e.g., in a relatively narrow beam extending substantially parallel to the central axis of the probe 1030, in a wider beam, and the like.

Alternatively, the probe 1020 may include other energy sources instead of the light transmitter 1038. For example, a source of electromagnetic energy, radiofrequency (RF) energy, vibrational energy, and the like (not shown) may be provided on the distal end 1024 of the probe 1020 for delivering energy pulses to activate the marker 40, as described elsewhere herein. The energy source(s) may be pulsed in a predetermined manner, e.g., to cause the circuits of the marker 40 to be alternately activated and deactivated.

The probe 1020 may include a processor within the display unit 1040 including one or more controllers, circuits, signal generators, gates, and the like (not shown) needed to generate signals for transmission by the transmit antenna and/or to process signals received from the receive antenna. The components of the processor may include discrete components, solid state devices, programmable devices, software components, and the like, as desired. For example, the probe 1020 may include an impulse generator, e.g., a pulse generator and/or pseudo noise generator (not shown), coupled to the transmit antenna to generate transmit signals, and an impulse receiver for receiving signals detected by the receive antenna. The processor may include a micro-controller and a range gate control that alternately activate the impulse generator and impulse receiver to transmit electromagnetic pulses, waves, or other signals via the transmit antenna, and then receive any reflected electromagnetic signals via the receive antenna, e.g., similar to other embodiments herein. Exemplary signals that may be used include microwave, radio waves, such as micro-impulse radar signals, e.g., in the ultralow bandwidth region.

The probe 1020 may be coupled to a display 1042 of the display unit 1040, e.g., by cables 1036, for displaying information to a user of the probe 1020, e.g., spatial or image data obtained via the antennas. Optionally, the probe 1020 may include other features or components, such as one or more user interfaces, memory, transmitters, receivers, connectors, cables, power sources, and the like (not shown). For example, the probe 1020 may include one or more batteries or other internal power sources for operating the components of the probe 1020. Alternatively, the probe 1020 may include a cable, such as one of the cables 1036, that may be coupled to an external power source, e.g., standard AC power, for operating the components of the probe 1020.

As shown in FIG. 6, the internal components of the probe 1020 may be provided in a housing or casing such that the probe 1020 is self-contained. For example, the casing may be relatively small and portable, e.g., such that the entire probe 1020 may be held in a user's hand. Optionally, a portion of the probe 1020 may be disposable, e.g., a portion adjacent the distal end 1024, or a disposable cover, sleeve, and the like (not shown) may be provided if desired, such that at least a proximal portion of the probe 1020 may be reusable, e.g., similar to other embodiments herein. Alternatively, the entire probe 1020 may be a disposable, single-use device while the display unit 1040 may be used during multiple procedures by connecting a new probe 1020 to the display unit 1040, which may remain out of the surgical field yet remain accessible and/or visible, as desired. Additional information on construction and/or operation of the probe 1020 may be found in the applications incorporated by reference elsewhere herein.

Figure 9:
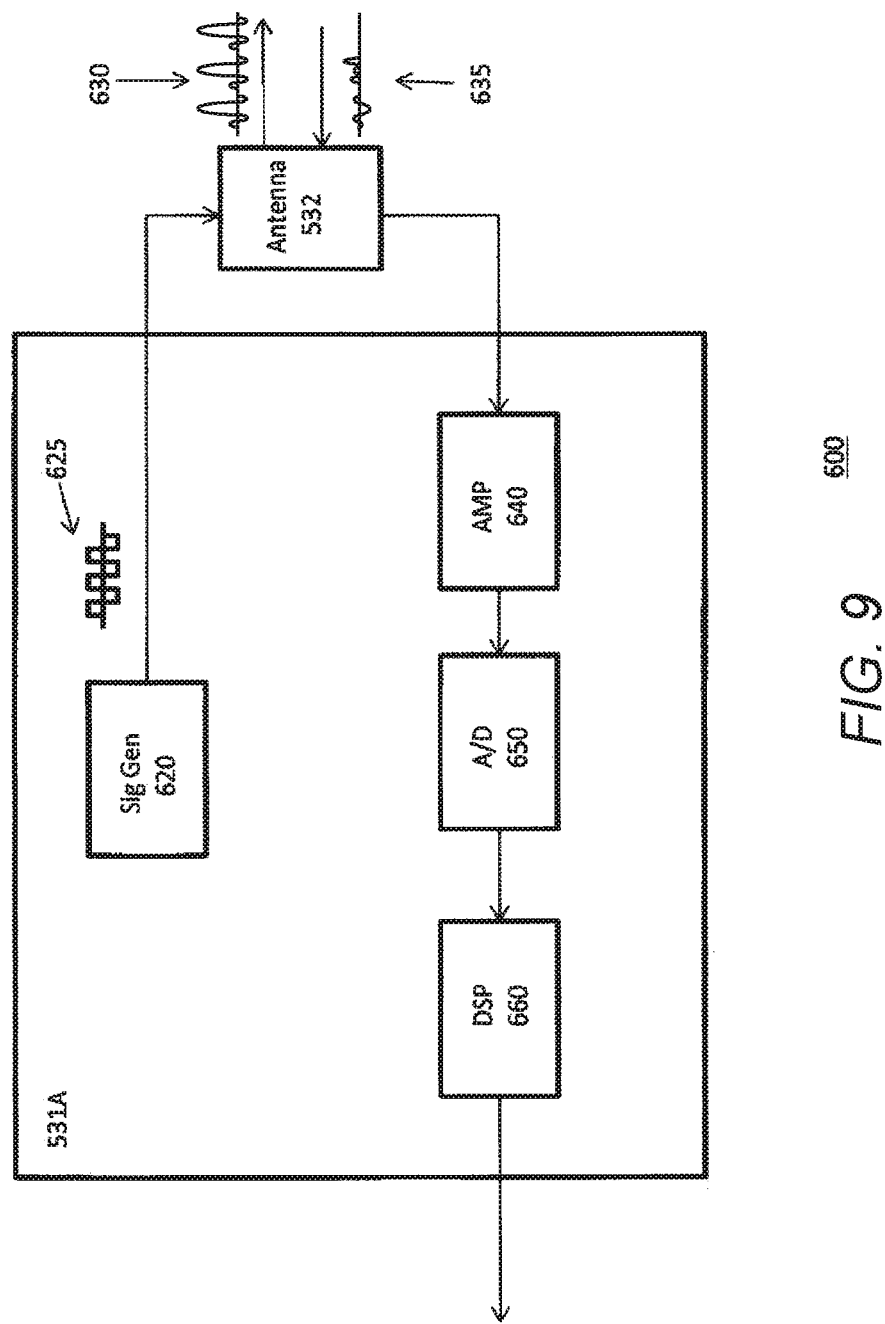
FIG. 9 is block diagram depicting exemplary components of the probe of FIG. 8.

FIG. 9 is a block diagram 600 showing exemplary components of the probe 1020 (although, alternatively, some of the components may be located within the display unit 1040 of FIG. 8). The probe 1020 may include a signal generator 620, an amplifier 640, an analog-to-digital (A/D) converter 650, and a digital signal processor (DSP) 660. The signal generator 620, e.g., a reference oscillator, produces an oscillating signal, such as a square wave signal, a triangular wave signal, or a sinusoidal signal.

For example, a square wave signal 625 may be sent from the signal generator 620 to the transmit antenna of the antenna portion 532 of the probe 1020. When the square wave signal 625 passes through the transmit antenna, the transmit antenna acts as a band pass filter ("BPF") and converts the square wave signal 625 to a series of pulses 630. As such, the transmit signal 1034T (shown in FIG. 6) transmitted by the probe 1020 includes a series of pulses 630. The transmit signals 1034T may be transmitted into the tissue and reflected from the marker 40 (as shown in FIG. 6), as represented by the receive signals 1034R. Once the transmit signal 1034T is reflected from the marker 40, the reflected signal (i.e., the receive signals 1034R) includes a series of attenuated pulses 635 (shown in FIG. 9).

The receive antenna of the antenna portion 532 of the probe 1020 may receive the receive signals 1034R (shown in FIG. 6). As shown in FIG. 9, the receive signals 1034R, which may include a series of attenuated pulses 635, may be inputted into an amplifier 640 in order to amplify the gain of the pulses 635. The output of the amplifier 640 may be inputted into an A/D converter 650 in order to convert the amplified analog signal into a digital signal. The digital signal output from the A/D converter 650 may be inputted into a DSP 660 for processing. The DSP 660 may perform a number of processing functions including, but not limited to, calculating a difference in time from the time the transmit signal 501 was sent to the time the receive signal 502 was received, determining the distance from the tip of the microwave antenna probe 531 to the marker 521, determining the location of the marker 40 in relation to the tip of the probe 1020, measuring the amplitude of the receive signals 1034R, and/or determining the direction the marker 40 is located in relation to the tip of the probe 1020, e.g., as described in the applications incorporated by reference herein. The output of the DSP 660 may be presented on the display 1042 of the display unit 1040.

Turning to FIGS. 10A-10D, an exemplary embodiment of an antenna probe 930 is shown that may be used in any of the systems and methods described elsewhere herein. Generally, the probe 930 includes a housing 940, an antenna subassembly 950, and shielding 980. Optionally, the probe 930 may include an outer sleeve or cover (not shown) surrounding one or more components of the probe 930, e.g., surrounding openings in the housing 940, for reducing contamination, exposure, and/or otherwise protecting the internal components of the probe 930.

Figure 11:
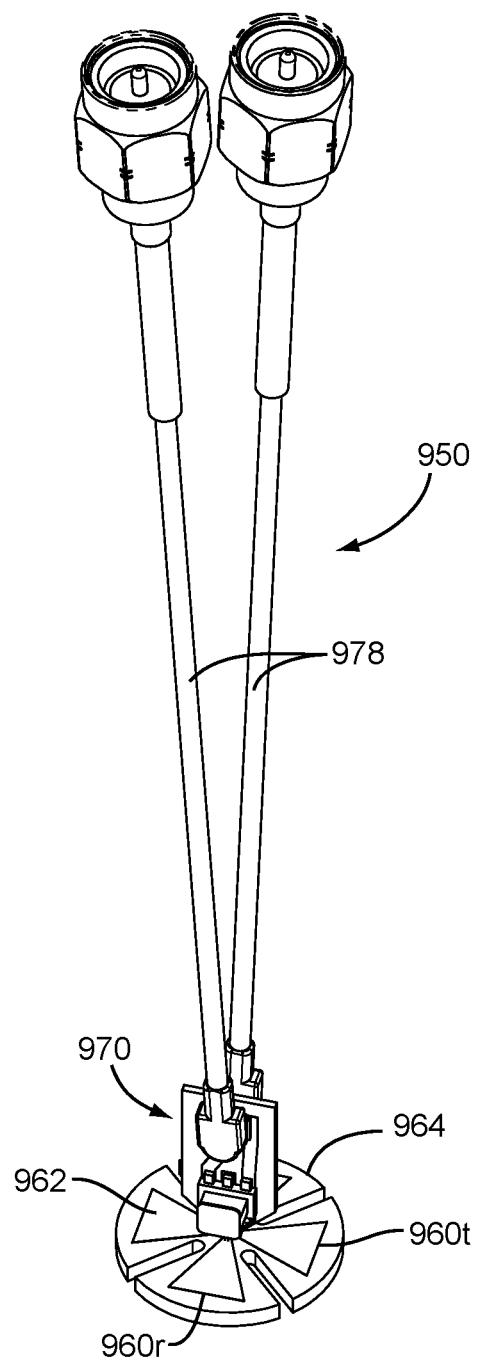
FIG. 11 is a perspective view of an antenna subassembly that may be included in the probe of FIG. 10A.
Figure 12A:
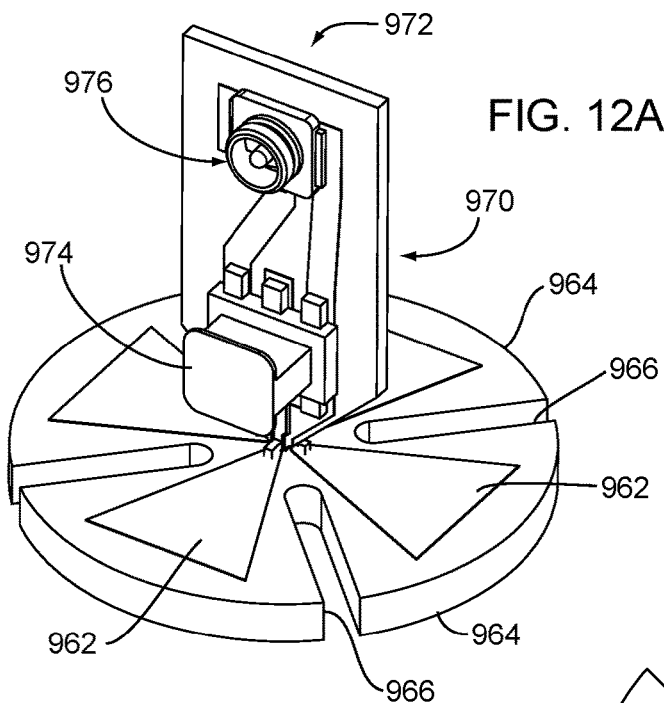
FIGS. 12A-12C are perspective, top, and bottom views, respectively, of the antenna elements of the antenna subassembly of FIG. 11.
Figure 12B:
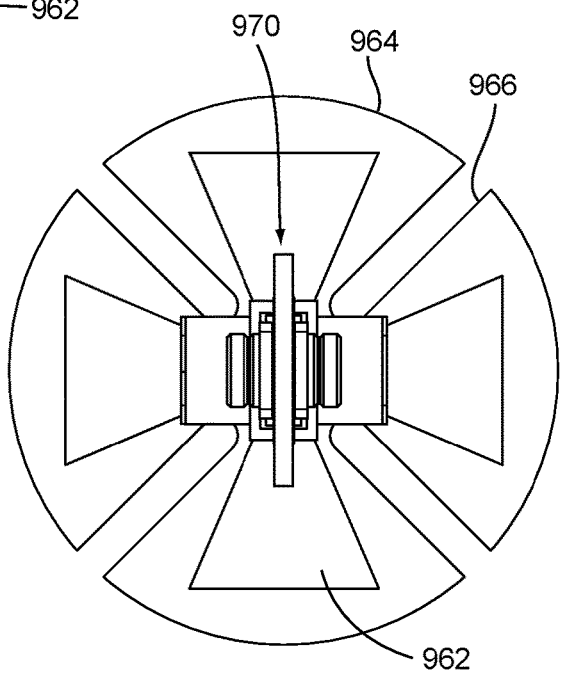
Figure 12C:
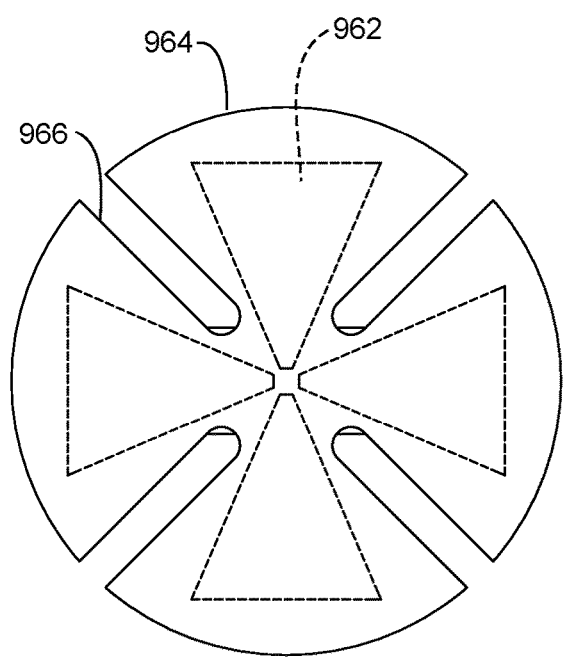

With additional reference to FIG. 11, the antenna subassembly 950 includes a transmit antenna 960t and a receive antenna 960r, each having a bowtie configuration, combined to form a Maltese cross antenna. As shown in FIGS. 12A-12C, each antenna 960 includes a pair of antenna elements 962 offset ninety degrees (90°) from one another on a disk or other base of dielectric material 964. Each of the antenna elements 962 may be formed separately and then attached to the disk 964 or may be deposited directly onto the disk 964. In an exemplary embodiment, the antenna elements 962 may be formed from silver film or other material deposited onto the top surface of ceramic disk 964.

Circuitry 970 may be coupled to the antennas 960, e.g., including a PCB 972 on which are provided one or more transformers 974 and connectors 976 coupled to the respective antenna elements 962 by appropriate leads. Coaxial cables 978 may be coupled to the connectors 976 to allow the antennas 960 to be coupled to other components of the system, similar to other embodiments described elsewhere herein.

As best seen in FIG. 12A-12C, the disk 964 includes a plurality of radial slots 966 between the antenna elements 962. Thus, the antenna elements 962 may be substantially isolated from one another by air within the slots 966, which may increase sensitivity, reduce crosstalk and/or other noise, and the like. Alternatively, the slots 966 may be filled with other insulating material, e.g., foam and the like (not shown), which may have a desired relatively low dielectric constant to substantially isolate the antenna elements 962 from one another.

Figures 10C, 10D:
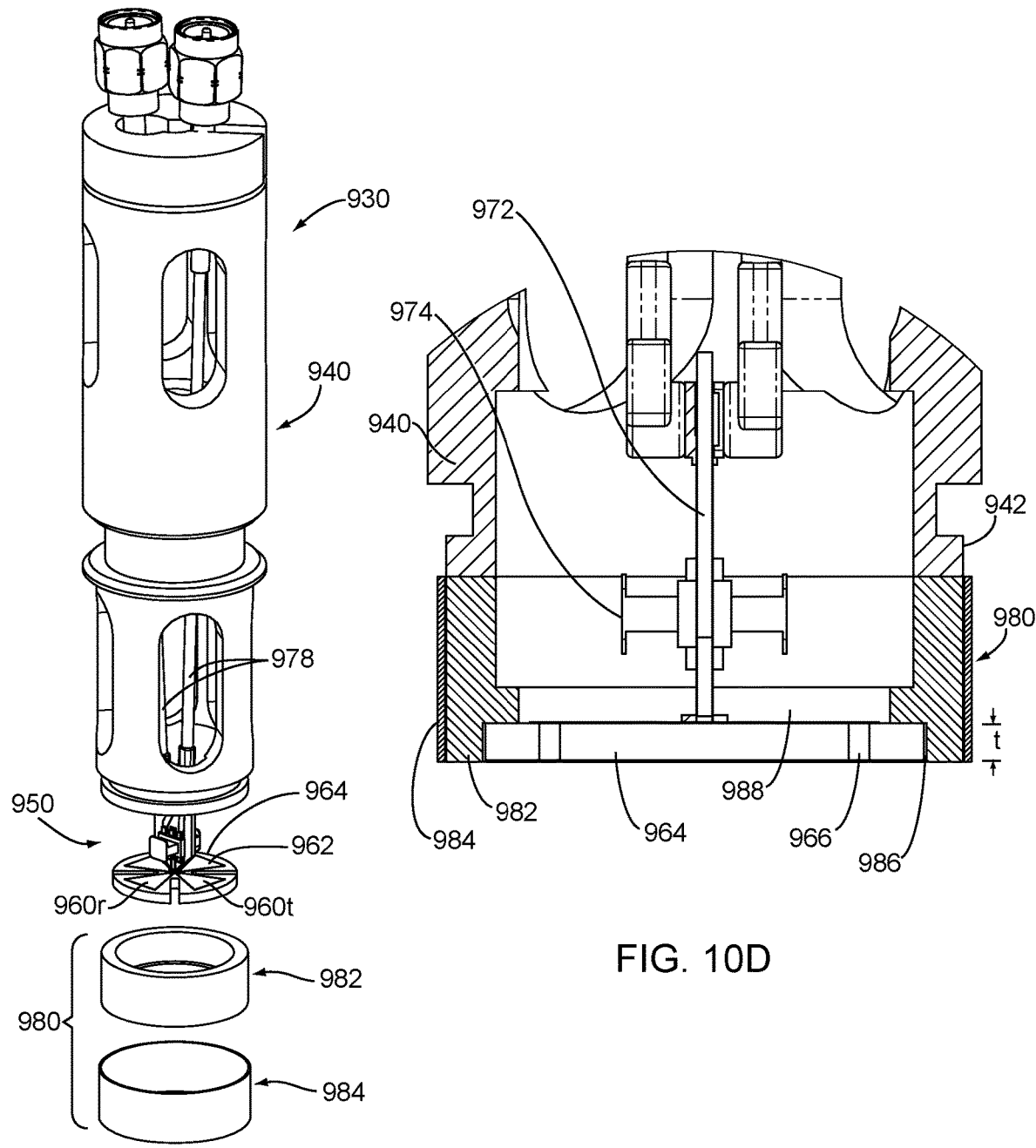
FIG. 10C is a partially exploded view of the probe of FIG. 10A.
FIG. 10D is a cross-section of the tip of the probe of FIG. 10A taken along line 10D-10D.

As best seen in FIG. 10D, the disk 964 may be mounted within the shielding 980, which may in turn, be coupled to the tip 942 of the housing 940, e.g., by one or more of bonding with adhesive, sonic welding, fusing, cooperating connectors (not shown), and the like. As shown, the shielding 980 includes an inner insulation layer, e.g., formed from a collar of nylon or other polymeric material, surrounded by a relatively thin outer shield 984, e.g., formed from copper or other material, to provide a Faraday shield. In an exemplary embodiment, a layer of copper tape may be wrapped around the inner shield 982 with the ends secured together. Alternatively, the outer shield 984 may be a sleeve of shielding material into which the inner shield 982 is inserted and attached, e.g., by bonding with adhesive, interference fit, and the like.

As shown in FIG. 10D, the shielding 980 may have a length substantially greater than the thickness "t" of the disk 964. For example, the inner shield 982 may include an annular recess 986 into which the disk 964 may be inserted and attached, e.g., by interference fit, bonding with adhesive, and the like. As shown, the bottom surface of the disk 964 may be substantially flush with the distal end of the shielding 980 such that the disk 964 may contact tissue during use, as described elsewhere herein. Optionally, a Mylar film or other relatively thin layer of material (not shown) may be provided over the bottom surface of the disk 964 and/or the shielding 980, e.g., to prevent fluids or other material entering the tip, reduce contamination, and/or otherwise protect the tip of the probe 930.

With continued reference to FIG. 10D, the top surface of the disk 964 (with the antenna elements 962, not shown, thereon) may be exposed to a region of air within the shielding 980. Because of the low dielectric constant of air, the transmission from the transmit antenna 960t is focused distally, i.e., towards the tissue contacted by the disk 964. With the material of the disk 964 chosen to substantially match the dielectric constant of tissue, the depth of transmission into the tissue may be enhanced. The air behind the disk 964 may minimize lost energy that would otherwise be emitted by the transmit antenna 960t away from the tissue. Similarly, the disk 964 may focus the sensitivity of the receive antenna 960r directed towards the tissue. The air behind the disk 964 within the shielding 980 (as well as the slots 966 between the antenna elements 962) may minimize crosstalk, noise and/or may otherwise enhance operation of the probe 930. Additional information regarding the probe 930 and/or alternative embodiments may be found in the applications incorporated by reference herein.

The system 1010 of FIG. 6 may be used during a medical procedure, for example, in a breast biopsy or lumpectomy procedure, e.g., to facilitate localization of a lesion or other target tissue region and/or to facilitate dissection and/or removal of a specimen from a breast 90 or other body structure. It should be noted that, although the system 1010 is described as being particularly useful in localization of breast lesions, the system 1010 may also be used in localization of other objects in other areas of the body, e.g., as described in the applications incorporated by reference herein.

Before the procedure, a target tissue region, e.g., a tumor or other lesion, may be identified using conventional methods. For example, a lesion (not shown) within a breast 90 may be identified, e.g., using mammography and/or other imaging, and a decision may be made to remove the lesion. The marker 40 may be implanted within the breast 90 within or adjacent the target lesion, e.g., using a needle or other delivery device, such as the delivery device 260 shown in FIGS. 5A and 5B.

Once the marker(s) 40 is implanted, as shown in FIG. 6, the probe 1020 may be placed against a patient's skin, e.g., against the breast 90. Signals from the antenna of the probe 1020 may be delivered along with pulsed light from the light source to cause the switch 54 to open and close as the marker 40 receives and reflects the signals back to the probe 1020. If there is substantial clutter, crosstalk, or other noise being received by the probe 1020, e.g., due to the probe antennas, tissue or other structures within the patient's body near the marker 40, and the like, the reflected signals from the two states (switch 54 open and closed) may be subtracted from one another, substantially eliminated the other noise, and allowing the probe 1020 to identify and/or locate the marker 40. Thus, the probe 1020 may use the modulated reflected signals to increase the signal-to-noise ratio of the signals.

The display 1042 may display information to the user to facilitate locating the marker 40 within the breast 90. For example, the display 1042 may simply be a readout providing distance, angle, orientation, and/or other data based on predetermined criteria, e.g., based on the relative distance from the marker 40 to the probe 1020. The distance information may be displayed as a numerical value representing the distance in units of length, such as in inches (in.) or centimeters (cm). In addition or alternatively, a speaker 1044 on the display unit 1040 may produce an audible indication of distance, e.g., spaced-pulses that increase in speed as the probe 1020 is closer to the marker 40. In another alternative, the display 1042 may present a graphical image (e.g., a two-dimensional or three-dimensional image) depicting the marker 40, the probe 1020, the distance from the probe 1020 to the marker 40, and/or a physiological picture of the body part containing the marker (e.g., the breast).

For example, as shown in FIG. 6, the distal end 1024 of the probe 1020 may be placed adjacent or in contact with the patient's skin, e.g., generally above the lesion, and/or otherwise aimed generally towards the lesion and marker 40, and activated. The transmit antenna (not shown) of the probe 1020 may emit electromagnetic signals 1034T that travel through the tissue and are reflected off of the marker 40. Return signals 1034R may be reflected back to the receive antenna (not shown) in the probe 1020, which may then determine a spatial relationship between the marker 40 and the distal end 1024 of the probe 1020, e.g., a distance and/or orientation angle, to facilitate determining a proper direction of dissection for the surgeon.

In addition, substantially simultaneously, the probe 1020 may transmit light pulses 1038a, which may be received by the diodes 52 of the marker 40 (not shown, see, e.g., FIGS. 3A and 3B). The diodes 52 may alternately generate a voltage, causing the switch 54 to open and close. This causes the marker 40 to change the phase of the signals reflected back to the probe 1020, which may process the signals, e.g., by subtraction, to identify and/or locate the marker 40, and consequently the target lesion.

Tissue may then be dissected, e.g., by creating an incision in the patient's skin and dissecting intervening tissue to a desired depth, e.g., corresponding to a target margin around the lesion is reached. A tissue specimen may be excised or otherwise removed using conventional lumpectomy procedures, e.g., with the marker 40 remaining within the removed specimen 1046.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A marker sized for introduction into a target tissue region within a patient's body, comprising:
   a field effect transistor (FET);
   one or more photosensitive diodes coupled in series across a source and a gate of the FET to convert light pulses received from a light source to generate a voltage to open and close the FET;
   a pair of elongate wires coupled to a drain of the FET and the source of the FET to provide an antenna, the FET configured to open and close to modulate signals reflected by the antenna back to a source of the signals; and an electro static discharge (ESD) protection device coupled between the drain and the source of the FET to set a maximal voltage between the drain and the source.

2. The marker of claim 1, wherein the pair of elongate wires comprise a first wire coupled to the drain of the FET and a second wire coupled to the source of the FET to provide the antenna such that when the FET is closed, the first and second wires are connected together.

3. The marker of claim 1, wherein the one or more photosensitive diodes comprise multiple diodes arranged orthogonally relative to one another.

4. The marker of claim 1, wherein the elongate wires are biased to a substantially straight configuration.

5. The marker of claim 1, wherein the elongate wires extend in generally opposite directions from a package containing the one or more photodiodes and the FET.

6. The marker of claim 1, further comprising a resistor coupled between the source and gate of the FET.

7. The marker of claim 1, wherein the wires are biased to assume a curvilinear configuration.

8. The marker of claim 1, wherein the wires are formed from elastic or superelastic material shape set such that the wires are biased to a helical configuration yet may be resiliently straightened to a substantially linear configuration to facilitate loading the marker into a delivery device.

9. A marker sized for introduction into a target tissue region within a patient's body, comprising:
 a field effect transistor (FET);
 one or more photosensitive diodes coupled in series across a source and a gate of the FET to convert light pulses received from a light source to generate a voltage to open and close the FET;
 a first wire coupled to one of a drain of the FET and the source of the FET to provide an antenna, the FET configured to open and close to modulate signals reflected by the antenna back to a source of the signals; and
 an electro static discharge (ESD) protection device coupled between the drain and the source of the FET to set a maximal voltage between the drain and the source.

10. The marker of claim 9, wherein the first wire is coupled to the drain of the FET, the marker further comprising a second wire coupled to the source of the FET.

11. The marker of claim 9, wherein the one or more photosensitive diodes comprise multiple diodes arranged orthogonally relative to one another.

12. The marker of claim 9, wherein the first wire is biased to a substantially straight configuration.

13. The marker of claim 9, further comprising a resistor coupled between the source and gate of the FET.

14. The marker of claim 9, wherein the first wire us biased to assume a curvilinear configuration.

15. The marker of claim 9, wherein the first wire is formed from elastic or superelastic material shape set such that the first wire is biased to a helical configuration yet may be resiliently straightened to a substantially linear configuration to facilitate loading the marker into a delivery device.

* * * * *